(12) United States Patent
Jor (10) Patent No.: US 12,403,229 B2
(45) Date of Patent: Sep. 2, 2025

(54) DIALYSIS DEVICE FOR USE WITH INTERFACE MEDIA, DIALYSIS SYSTEMS, USE OF DIALYSIS DEVICE, METHOD FOR ESTABLISHING DIALYSIS SYSTEM, METHOD FOR FILLING AND/OR PRIMING DIALYSIS SYSTEM AND METHOD FOR REMOVING AIR FROM DIALYSIS SYSTEM

(71) Applicant: Fresenius Medical Care Deutschland GmbH, Bad Homburg (DE)

(72) Inventor: Kee Jor, Hong Kong (CN)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 270 days.

(21) Appl. No.: 17/280,621

(22) PCT Filed: Sep. 29, 2018

(86) PCT No.: PCT/CN2018/108602
§ 371 (c)(1),
(2) Date: Mar. 26, 2021

(87) PCT Pub. No.: WO2020/062135
PCT Pub. Date: Apr. 2, 2020

(65) Prior Publication Data
US 2021/0338910 A1    Nov. 4, 2021

(51) Int. Cl.
*A61M 1/16* (2006.01)
*A61M 1/34* (2006.01)
(52) U.S. Cl.
CPC ........ *A61M 1/1639* (2014.02); *A61M 1/1633* (2014.02); *A61M 1/1692* (2013.01);
(Continued)
(58) Field of Classification Search
None
See application file for complete search history.

(56) References Cited

U.S. PATENT DOCUMENTS

| 3,682,172 A | 8/1972 | Freedman et al. |
| 3,839,200 A | 10/1974 | Gigou et al. |

(Continued)

FOREIGN PATENT DOCUMENTS

| CA | 2518969 A1 | 9/2004 |
| CN | 1761494 A | 4/2006 |

(Continued)

OTHER PUBLICATIONS

Extended European Search Report in European Appln. No. 18935132.3, dated Apr. 8, 2022, 11 pages.

(Continued)

*Primary Examiner* — Krishnan S Menon
(74) *Attorney, Agent, or Firm* — Fish & Richardson P.C.

(57) ABSTRACT

A dialysis device comprises at least a first membrane and a second membrane, wherein a first chamber formed by the first membrane is configured to receive a first fluid; a second chamber formed by the second membrane is configured to receive a second fluid; a third chamber formed in between a housing, the first membrane and the second membrane is configured to receive a third fluid; the first fluid flowing through the first membrane can be indirectly communicated with the second fluid flowing through the second membrane via the third fluid. A dialysis system, use of the dialysis device, a method for establishing the dialysis system, a method for filling and/or priming the dialysis system and a method for removing air are further disclosed. The dialysis device and the dialysis system are suitable for viscous biological dialysis fluid and no direct flow occurs between the patient and the dialysis fluid.

7 Claims, 6 Drawing Sheets

(52) U.S. Cl.
CPC .......... *A61M 1/1696* (2013.01); *A61M 1/341* (2014.02); *A61M 2205/3334* (2013.01)

(56) References Cited

U.S. PATENT DOCUMENTS

| | | | | |
|---|---|---|---|---|
| 4,784,768 | A * | 11/1988 | Mathieu | B01D 63/04 |
| | | | | 210/336 |
| 6,271,023 | B1 * | 8/2001 | Baurmeister | B01D 63/026 |
| | | | | 210/321.64 |
| 9,345,825 | B2 | 5/2016 | Herrenbauer et al. | |
| 10,792,412 | B2 | 10/2020 | Kloeffel et al. | |
| 2015/0258268 | A1 | 9/2015 | Collier et al. | |
| 2017/0056576 | A1 * | 3/2017 | Doyle | A61M 1/3479 |
| 2017/0189599 | A1 | 7/2017 | Menzel Bueno et al. | |

FOREIGN PATENT DOCUMENTS

| | | |
|---|---|---|
| CN | 102458501 A | 5/2012 |
| CN | 203989191 U | 12/2014 |
| CN | 106693097 A | 5/2017 |
| CN | 107921194 A | 4/2018 |
| DE | 19624250 | 1/1998 |

OTHER PUBLICATIONS

PCT International Search Report and Written Opinion in International Appln. No. PCT/CN2018/108602, mailed Jun. 27, 2019, 10 pages.

* cited by examiner

DIALYSIS DEVICE FOR USE WITH INTERFACE MEDIA, DIALYSIS SYSTEMS, USE OF DIALYSIS DEVICE, METHOD FOR ESTABLISHING DIALYSIS SYSTEM, METHOD FOR FILLING AND/OR PRIMING DIALYSIS SYSTEM AND METHOD FOR REMOVING AIR FROM DIALYSIS SYSTEM

CROSS-REFERENCE TO RELATED APPLICATIONS

The present application is the national stage entry of International Patent Application No. PCT/CN2018/108602, filed on Sep. 29, 2017, the disclosure of which is incorporated herein by reference.

TECHNICAL FIELD

The disclosure relates to an innovative indirect dialysis method with interface media, a dialysis device, dialysis systems, use of at least one dialysis device, a method for establishing the dialysis system, a method for filling and/or priming the dialysis system and a method for removing air from the dialysis system, especially relates to a dialyzer for use with the interface media, a dialysis method with the interface media and a corresponding apparatus, a dual-dialyzer treatment method and a corresponding apparatus, a balanced circulation hydraulic for a dual-dialyzer treatment apparatus.

BACKGROUND ART

Hemodialysis is a procedure for removing toxic substances and metabolites normally removed by the kidneys, and for aiding in regulation of fluid and electrolyte balance. Hemodialysis is usually accomplished by a dialysis machine using dialysis fluid. Typical dialysis treatment requires around 120 L of dialysis fluid.

As an important part of the dialysis machine, a common dialyzer consists of a bundle of hollow fibers to increase membrane area. Fresh dialysis fluid passes through outer surfaces of the hollow fibers to remove wastes from blood via a dialysis process.

At present, a biological dialysis fluid resembling blood composition with plasma, blood cells and platelets is used in place of the conventional dialysis fluid. Such biological dialysis fluid can be recycled indefinitely through an active biological regeneration device to perform the dialysis treatment continuously. In this case, only small amount of dialysis fluid is needed.

Similar to blood, the biological dialysis fluid is viscous and it is more resistant to flow than the conventional dialysis fluid. The amount available in the treatment process is limited. Furthermore, it is subject to clotting at slow speed in a flow path. Conventional dialyzer and dialysis system are therefore not suitable for the following reasons:

Appfibers will compromise treatment efficiency.
2. Stagnant and congested area is subject to risk of clotting which will further compromise treatment efficiency. Flow along space in-between hollow fibers will possibly be blocked during the dialysis treatment. Effective biological dialysis fluid flow and interface for the dialysis treatment will be reduced. For the same reason, significant amount of biological dialysis fluid might then be stuck inside the dialyzer and can no longer be returned for regeneration.
3. Dialysate side compartment fluid volume is larger than blood side compartment.
4. Commonly used polysulfone hollow fiber membrane has asymmetrical structure. Relatively loose outer surface structure is not designed for blood-like fluid.
5. Safety risk in relation to membrane rupture is undetectable. It is especially dangerous when the dialysis fluid contains blood components.

In view of the above, an innovative solution is required to carry out the dialysis treatment safely and effectively for the blood-like biological dialysis fluid.

SUMMARY OF THE DISCLOSURE

In view of the problems existing in the prior art, an object of the disclosure is to provide a dialysis device, dialysis systems, use of at least one dialysis device, a method for establishing the dialysis system, a method for filling and/or priming the dialysis system and a method for removing air from the dialysis system.

For achieving this object, in the first aspect, provided is a dialysis device, comprising at least a first membrane and a second membrane, wherein a first chamber formed by the first membrane is configured to receive a first fluid; a second chamber formed by the second membrane is configured to receive a second fluid; a third chamber formed in between a housing, the first membrane and the second membrane is configured to receive a third fluid; and the first fluid flowing through the first membrane can be indirectly communicated with the second fluid flowing through the second membrane via the third fluid.

According to an optional embodiment, the first membrane and/or the second membrane is selected from a membrane formed by hollow fibers, a flat membrane, a spiral membrane or a cylindrical membrane.

According to an optional embodiment, the first membrane comprises at least a first group of hollow fiber; and the second membrane comprises at least a second group of hollow fibers.

According to an optional embodiment, the first group of hollow fibers and the second group of hollow fibers each are configured as a separate bundle of hollow fibers respectively; or at least a portion of the first group of hollow fibers is surrounded by at least a portion of the second group of hollow fibers; preferably, at least one subgroup of the first group of hollow fibers is surrounded by at least one subgroup of the second group of hollow fibers; preferably, at least one subgroup of the first group of hollow fibers and at least one subgroup of the second group of hollow fibers are alternatively arranged; preferably, at least one row of subgroups of the first group of hollow fibers and at least one row of subgroups of the second group of hollow fibers are alternatively arranged; and/or, preferably, at least one column of subgroups of the first group of hollow fibers and at least one column of subgroups of the second group of hollow fibers are alternatively arranged.

According to an optional embodiment, the number, material, structure and manufacturing process of the first group of hollow fibers can be the same as or different from those of the second group of hollow fibers.

According to an optional embodiment, the first fluid is a patient's or animal's blood to be treated; the second fluid is a biological dialysis fluid; and/or the third fluid is an electrolyte solution, preferably a saline solution working as an interface media.

According to an optional embodiment, the dialysis device further comprises: at least a first pair of ports configured to be communicated with the first chamber; at least a second pair of ports configured to be communicated with the second chamber; and/or at least a third pair of ports configured to be communicated with the third chamber.

According to an optional embodiment, a direction of the first fluid flowing through the first group of hollow fibers is opposite to that of the second fluid flowing through the second group of hollow fibers; and/or the third fluid is fully filled in the third chamber, preferably flows in a circulation loop.

In the second aspect, provided is use of at least one dialysis device.

In the third aspect, provided is a dialysis system, comprising at least one dialysis device.

According to an optional embodiment, the dialysis system further comprises: at least one detector configured to detect blood leak into the third fluid; a driving device, preferably a pump, configured to generate a circulation flow of the third fluid through the third chamber; and/or a fluid regeneration device configured to regenerate a fresh second fluid after passing through the second chamber.

In the fourth aspect, provided is a dialysis system, comprising at least a first dialysis device and a second dialysis device, wherein a first chamber formed by a first membrane is configured to receive a first fluid; a second chamber is formed in between a first housing of the first dialysis device and the first membrane; a third chamber formed by a second membrane is configured to receive a second fluid; a fourth chamber is formed in between a second housing of the second dialysis device and the second membrane; and the second chamber and the fourth chamber are configured to receive a third fluid, and the first fluid flowing through the first membrane can be indirectly communicated with the second fluid flowing through the second membrane via the third fluid.

According to an optional embodiment, the dialysis system further comprises: a circulation means, configured to fluidly connect the second chamber with the fourth chamber for circulating the third fluid; and/or a driving device, preferably a pump, configured to generate a circulation flow of the third fluid between the second chamber and the fourth chamber.

According to an optional embodiment, the circulation means further comprises at least one detector configured to detect blood leak into the third fluid; preferably at least two detectors, one of which is configured to detect blood leak into the third fluid output from the second chamber and the other of which is configured to detect blood leak into the third fluid output from the fourth chamber.

According to an optional embodiment, the dialysis system further comprises: a fluid regeneration device configured to regenerate a fresh second fluid after passing through the third chamber; and/or an ultrafiltration means, preferably an ultrafiltration pump, configured to control a volume of ultrafiltration.

According to an optional embodiment, the first dialysis device can be the same as or different from the second dialysis device.

According to an optional embodiment, the circulation means further comprises at least a balancing device, configured to balance the fluid flowing the second chamber and the fourth chamber to keep the third fluid flow in a closed system; preferably, the balancing device has a single balancing chamber, which comprises a first balancing compartment and a second balancing compartment; or the balancing device has dual balancing chambers, each of which comprises a first balancing compartment and a second balancing compartment.

According to an optional embodiment, the circulation means further comprises: an air detection means, configured to detect the presence of air in an air separation chamber, preferably and connected fluidly in a circulation loop of the third fluid, wherein the air separation chamber is configured to remove the air from the air separation chamber after the air is detected, preferably the air detection means is disposed or integrated in the air separation chamber; and/or a container fluidly connected with a circulation loop of the third fluid and configured to provide a fresh third fluid; preferably, the third fluid is on-line generated.

In the fifth aspect, provided is a method for establishing the dialysis system.

In the sixth aspect, provided is a method for filling and/or priming the dialysis system.

According to an optional embodiment, the method further comprises: filling the third fluid in a circulation loop of the third fluid with balance chamber fluid volume; and circulating the third fluid in the circulation loop for preset cycles per minute; preferably, repeating the filling and the circulating to refresh the third fluid in the circulation loop.

In the seventh aspect, provided is a method for removing air from the dialysis system.

According to an optional embodiment, the method further comprises: turning off the balancing device on completion of a current cycle after air is detected; and filling a fresh third fluid in the air separation chamber until no air is detected.

According to the present disclosure, the dialysis device and the dialysis system are suitable for using the viscous biological dialysis fluid and no direct flow between the patient and the biological dialysis fluid allows safer isolation in case abnormality is detected.

BRIEF DESCRIPTION OF THE DRAWINGS

The disclosure and advantages thereof will be further understood by reading the following detailed description of some preferred exemplary embodiments with reference to the drawings in which.

DETAILED DESCRIPTION OF PREFERRED EMBODIMENTS

Some exemplary embodiments of the present disclosure will be described hereinafter in more details with reference to the drawings to better understand the basic concept and various advantages of the disclosure.

Figure 1:
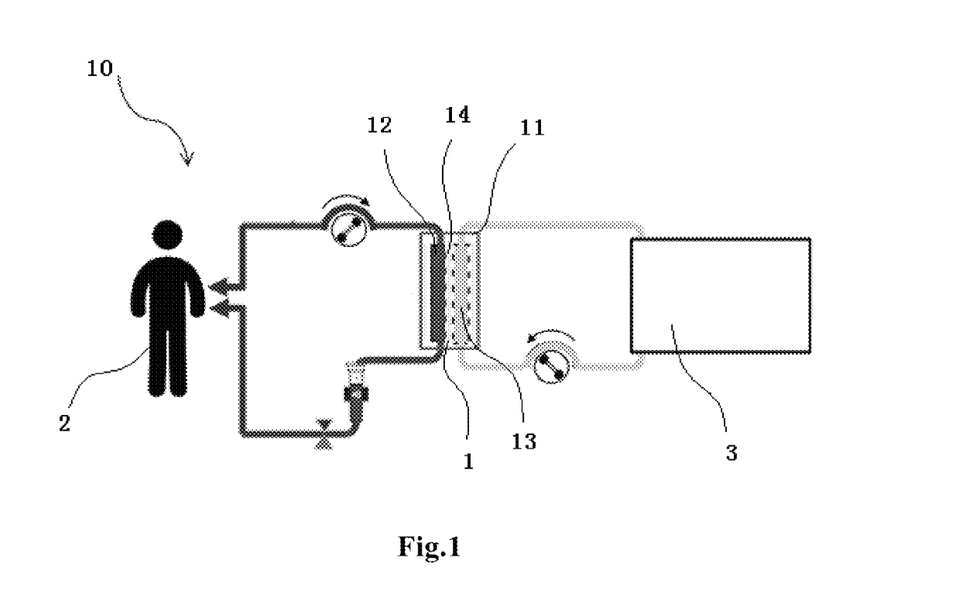
FIG. 1 schematically shows a dialysis system comprising a dialysis device according to an exemplary embodiment of the present disclosure.
Figure 2:
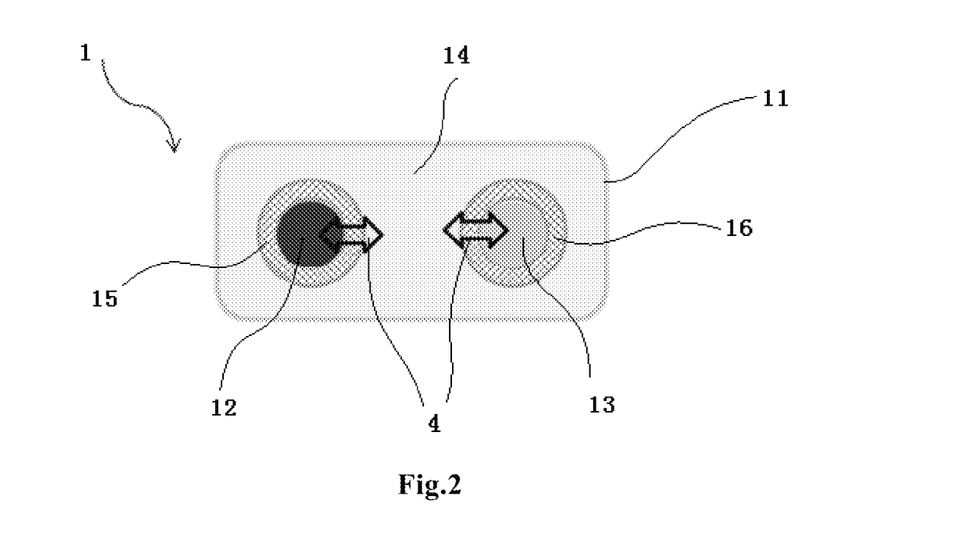
FIG. 2 shows a sectional view of the dialysis device in FIG. 1.

FIG. 1 schematically shows a dialysis system 10 comprising a dialysis device 1 according to an exemplary embodiment of the present disclosure, to better explain operational principle of the dialysis device 1. FIG. 2 shows a sectional view of the dialysis device 1.

As shown in FIG. 1 and FIG. 2, the dialysis device 1 comprises a housing 11, a first chamber 12, a second chamber 13 and a third chamber 14. The housing 11 can be configured as a cylinder for a common existing dialyzer or formed as a column with a rectangular cross-section and the like. The first chamber 12 is formed by a first membrane 15, the second chamber 13 is formed by a second membrane 16, and the third chamber 14 is formed in between the housing 11, the first membrane 15 and the second membrane 16.

The first chamber 12 is configured to receive a first fluid, the second chamber 13 is configured to receive a second fluid, and the third chamber 14 is configured to receive a third fluid, wherein the first fluid flowing through the first membrane 15 can be indirectly communicated with the second fluid flowing through the second membrane 16 via the third fluid. Therefore, the dialysis device 1 operates with interface media.

For example, in the dialysis system 10 shown in FIG. 1, the first chamber 12 is fluidly connected to a patient 2 to receive blood to be treated, the second chamber 13 is fluidly connected with a biological dialysis fluid device 3 to receive biological dialysis fluid from the biological dialysis fluid device 3, and the third chamber 14 is filled with the third fluid. In this case, the first fluid is the blood to be treated, the second fluid is the biological dialysis fluid, for example a dialysis solution or normal blood, and a dialysis process is done indirectly via the third fluid working as the interface media, i.e. the blood against the interface media, then the interface media against the biological dialysis fluid and vice versa, which is schematically shown by two bidirectional arrows 4.

With this arrangement, a flow path for the biological dialysis fluid may be identical to an even flow path for the blood to minimize stagnant flow problem within the dialysis device 1. In addition, a volume of the biological dialysis fluid in the flow path inside the second chamber 13 can also be optimized as desired.

According to one exemplary embodiment of the present disclosure, the third fluid is an electrolyte solution, preferably a saline solution.

According to one exemplary embodiment of the present disclosure, the first membrane 15 and/or the second membrane 16 may be selected from a membrane formed by hollow fibers, a flat membrane or a spiral membrane or a cylindrical membrane.

For example, the first membrane 15 may comprise or consist of a first group of hollow fibers, and the second membrane 16 may comprise or consist of a second group of hollow fibers. In this case, the first chamber 12 may be formed by interior cavities of the first group of hollow fibers, and the second chamber 13 may be formed by interior cavities of the second group of hollow fibers.

Figure 3:
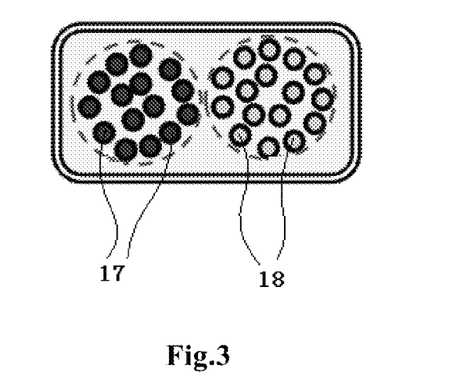
FIG. 3 shows an arrangement of a first group of hollow fibers and a second group of hollow fibers within a housing according to an exemplary embodiment of the present disclosure.

FIG. 3 shows an arrangement of the first group of hollow fibers and the second group of hollow fibers within the housing 11 according to an exemplary embodiment of the present disclosure.

As shown in FIG. 3, the first group of hollow fibers 17 and the second group of hollow fibers 18 each are configured as a respective separate bundle of hollow fibers.

Figure 4:
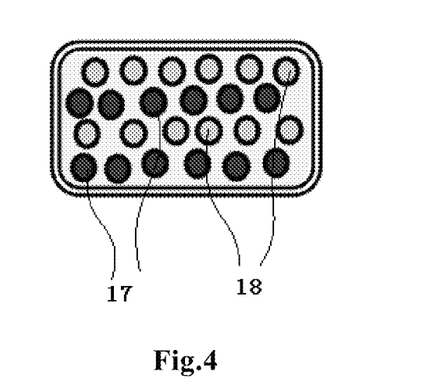
FIG. 4 shows an arrangement of the first group of hollow fibers and the second group of hollow fibers within the housing according to another exemplary embodiment of the present disclosure.

FIG. 4 shows an arrangement of the first group of hollow fibers 17 and the second group of hollow fibers 18 within the housing 11 according to another exemplary embodiment of the present disclosure.

As shown in FIG. 4, at least one subgroup of the first group of hollow fibers 17 and at least one subgroup of the second group of hollow fibers 18 are alternatively arranged within the housing 11.

Figure 5:
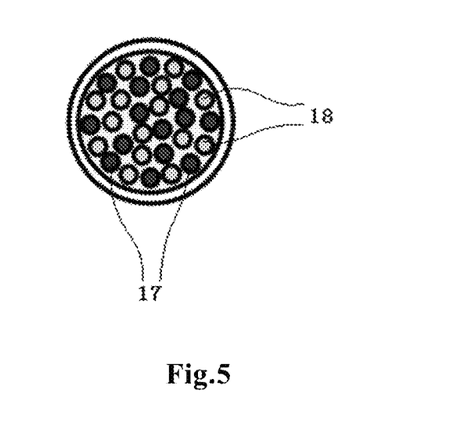
FIG. 5 shows an arrangement of the first group of hollow fibers and the second group of hollow fibers within the housing according to a further exemplary embodiment of the present disclosure.

FIG. 5 shows an arrangement of the first group of hollow fibers 17 and the second group of hollow fibers 18 within the housing 11 according to a further exemplary embodiment of the present disclosure.

As shown in FIG. 5, the first group of hollow fibers 17 and the second group of hollow fibers 18 are arranged within the housing 11 in an interleaving manner. Herein, the housing 11 has a circular cross section.

It may be understood by the skilled person in the art that the housing 11 may have any suitable shape.

It also may be understood by the skilled person in the art that the first group of hollow fibers 17 and the second group of hollow fibers 18 also may be arranged within the housing 11 in any other suitable manner.

For example, the arrangement of the first group of hollow fibers 17 and the second group of hollow fibers 18 within the housing 11 also may be any one or any combination of the following arrangements: 1) the first group of hollow fibers is surrounded by the second group of hollow fibers; 2) at least one subgroup of the first group of hollow fibers is surrounded by at least one subgroup of the second group of hollow fibers; 3) at least one row of subgroups of the first group of hollow fibers and at least one row of subgroups of the second group of hollow fibers are alternatively arranged; and 4) at least one column of subgroups of the first group of hollow fibers and at least one column of subgroups of the second group of hollow fibers are alternatively arranged.

According to an exemplary embodiment of the present disclosure, the number, material, structure and manufacturing process of the first group of hollow fibers 17 can be the same as or different from those of the second group of hollow fibers 18.

According to an exemplary embodiment of the present disclosure, the dialysis device 1 further comprises: at least a first pair of ports configured to be communicated with the first chamber 12; at least a second pair of ports configured to be communicated with the second chamber 13; and/or at least a third pair of ports configured to be communicated with the third chamber 14.

Figure 6:
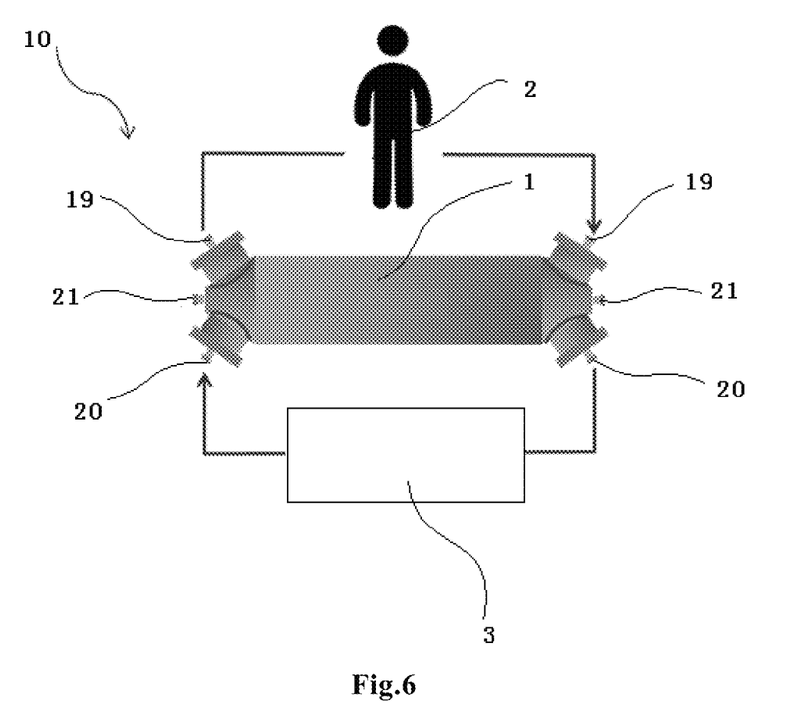
FIG. 6 shows a dialysis system comprising the dialysis device.

For example, FIG. 6 shows a dialysis system comprising the dialysis device 1, wherein the dialysis device 1 comprises a first pair of ports 19 configured to be communicated with the first chamber 12, a second pair of ports 20 configured to be communicated with the second chamber 13 and a third pair of ports 21 configured to be communicated with the third chamber 14.

Preferably, one of the first pair of ports 19, one of the second pair of ports 20 and one of the third pair of ports 21 are disposed at one end of the housing 11, and the other of the first pair of ports 19, the other of the second pair of ports 20 and the other of the third pair of ports 21 are disposed at the other opposite end of the housing 11.

As shown in FIG. 6, a direction of the first fluid, for example the blood, flowing through the first chamber 12, for example the first group of hollow fibers 17 is opposite to a direction of the second fluid, for example the biological dialysis fluid, flowing through the second chamber 13, for example the second group of hollow fibers 18, which can improve treatment efficiency.

According to an exemplary embodiment of the present disclosure, one of the third pair of ports 21 may be fluidly connected to an interface media fluid bag to carry out priming and filling process. For example, the interface media fluid bag may be suspended on an IV pole. After the process is done, the port may be closed to prepare for the dialysis treatment.

According to an exemplary embodiment of the present disclosure, the third fluid is fully filled in the third chamber 14. Further preferably, the third fluid flows in a circulation loop.

It also may be understood by the skilled person in the art that the dialysis device 1 may be used to but not limited to treat blood of an animal with fresh blood from a healthy animal of the same or probably different specie by means of dialysis treatment and the blood can be returned and regenerated by the healthy animal itself.

Figure 7:
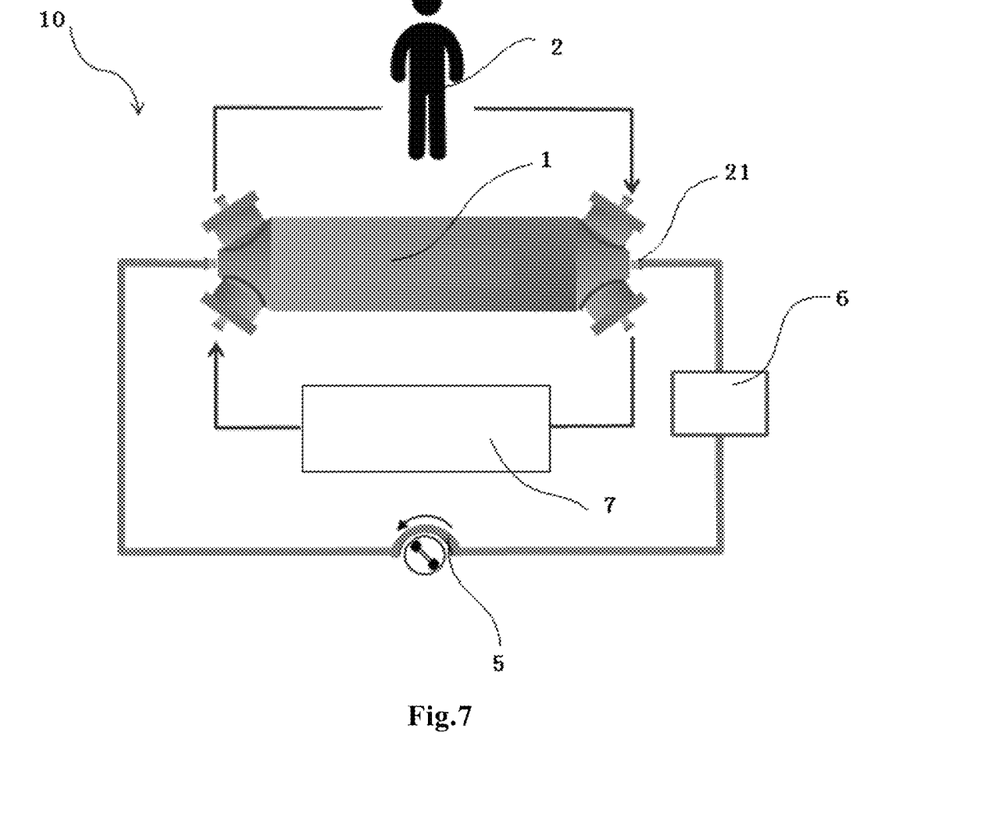
FIG. 7 shows another exemplary embodiment of the dialysis system.

FIG. 7 shows another exemplary embodiment of the dialysis system 10. As shown in FIG. 7, the dialysis system 10 further comprises a driving device 5, preferably a pump, configured to generate a circulation flow of the third fluid through the third chamber 14; and/or at least one detector 6, configured to detect blood leak into the third fluid.

It may be understood easily that the driving device 5 can improve treatment efficiency and the detector 6 can provide a safety measure. For example, if membrane rupture is detected by the detector 6, a patient blood pump will be stopped with a venous clamp closed to end the treatment safely.

According to one exemplary embodiment of the present disclosure, the detector 6 is disposed in a flow path between the driving device 5 and an outlet, i.e. the right port in FIG. 6, of the third pair of ports 21.

According to one exemplary embodiment of the present disclosure, the dialysis system 10 further comprises a fluid regeneration device 7 configured to regenerate a fresh second fluid after passing through the second chamber 14.

It should be noted that the biological dialysis fluid device 3 may be configured as a fluid regeneration device.

Figure 8:
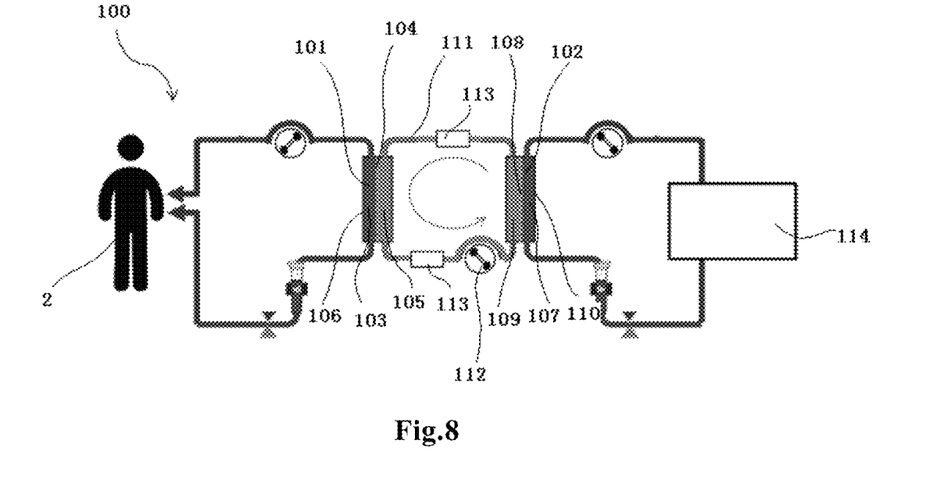
FIG. 8 shows a dialysis system according to an exemplary embodiment of the present disclosure.

FIG. 8 shows another dialysis system 100 according to an exemplary embodiment of the present disclosure.

As shown in FIG. 8, the dialysis system 100 comprises at least a first dialysis device 101 and a second dialysis device 102, wherein a first chamber 103 is formed by a first membrane 104 and configured to receive a first fluid, a second chamber 105 is formed in between a first housing 106 of the first dialysis device 101 and the first membrane 104, a third chamber 107 is formed by a second membrane 108 and configured to receive a second fluid, a fourth chamber 109 is formed in between a second housing 110 of the second dialysis device 102, the second chamber 105 and the fourth chamber 109 are configured to receive a third fluid, and the first fluid flowing through the first membrane 104 can be indirectly communicated with the second fluid flowing through the second membrane 108 via the third fluid.

According to one exemplary embodiment of the present disclosure, the dialysis system 100 further comprises a circulation means 111, configured to fluidly connect the second chamber 105 with the fourth chamber 109 for circulating the third fluid; and/or a driving device 112, preferably a pump, configured to generate a circulation flow of the third fluid between the second chamber 105 and the fourth chamber 109.

According to one exemplary embodiment of the present disclosure, the circulation means 111 further comprises at least one detector 113 configured to detect blood leak into the third fluid.

According to one exemplary embodiment of the present disclosure, the circulation means 111 comprises at least two detectors 113, one of which is configured to detect blood leak into the third fluid output from the second chamber 105 and the other of which is configured to detect blood leak into the third fluid output from the fourth chamber 109. Therefore, it is possible to detect more rapidly any blood leak into the third fluid to take safety measure in time.

For example, one detector 113 is disposed at or adjacent to an outlet port of the second chamber 105, and/or the other detector 113 is disposed at or adjacent to an outlet port of the fourth chamber 109.

According to one exemplary embodiment of the present disclosure, the dialysis system 100 further comprises a fluid regeneration device 114, configured to regenerate a fresh second fluid after passing through the third chamber 107.

According to one exemplary embodiment of the present disclosure, the first dialysis device 101 can be the same as or different from the second dialysis device 102. Preferably, the first dialysis device 101 and/or the second dialysis device 102 may be a conventional standard dialyzer.

Similarly, the first fluid may be a patient's or animal's blood to be treated, the second fluid may be a biological dialysis fluid; and/or the third fluid may be an electrolyte solution, preferably a saline solution working as an interface media.

Figure 9:
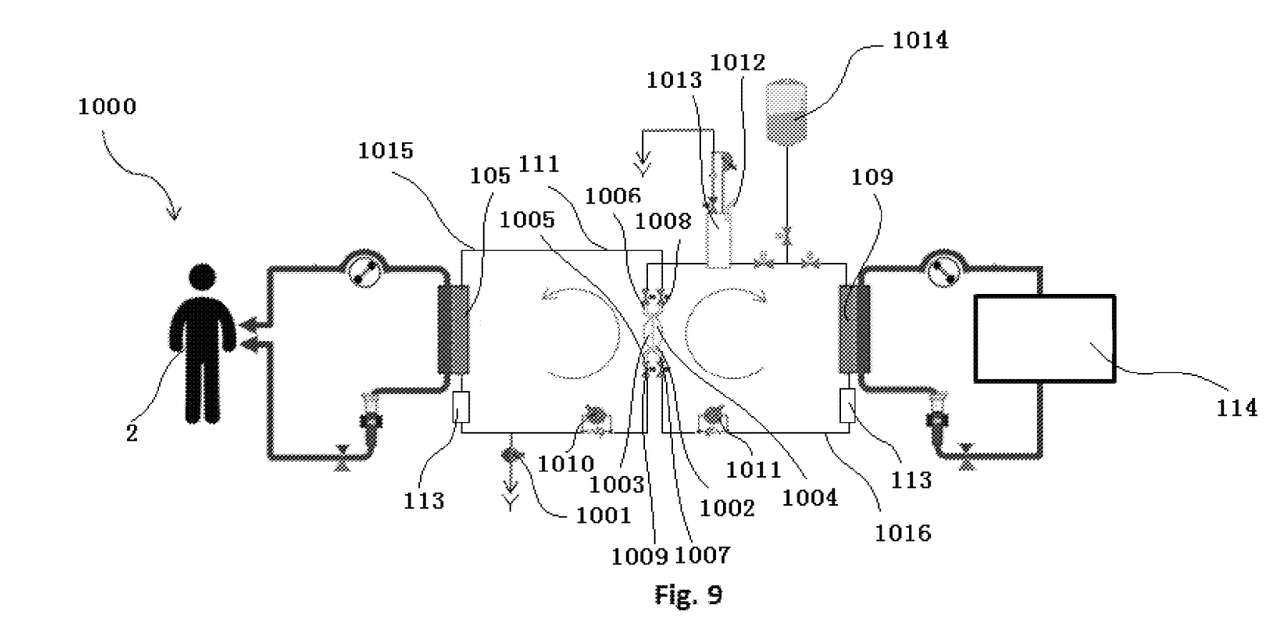
FIG. 9 shows another dialysis system according to an exemplary embodiment of the present disclosure.

FIG. 9 shows another dialysis system 1000 according to an exemplary embodiment of the present disclosure.

Below, differences between the dialysis system 100 and the dialysis system 1000 will described mainly.

According to one exemplary embodiment of the present disclosure, the dialysis system 1000 comprises an ultrafiltration means 1001, preferably an ultrafiltration pump, configured to control a volume of ultrafiltration. Balance of the fluid flowing in the second chamber 105 and the fourth chamber 109 is achieved by a balancing device 1002 to keep the third fluid flow in a closed system. The skilled person in the art will appreciate the balancing chamber concept as applied in typical dialysis machine design. The ultrafiltration means 1001 is applied to patient side only and is preferably connected fluidly in a circulation loop of the third fluid in connection with the second chamber 105.

According to one exemplary embodiment of the present disclosure, the circulation means 111 comprises the balancing device 1002 to direct fluid flow on patient side and dialysate fluid regeneration device side alternatively. During each cycle, dispensed fluid from the second chamber 105 will be exchanged with regenerated fluid from the fourth chamber 109.

As shown in FIG. 9, the balancing device 1002 may have or is a single balancing chamber, which comprises a first balancing compartment and a second balancing compartment 1004.

The single balancing chamber has a first inlet port 1005 and a first outlet port 1006 communicated with the first balancing compartment and a second inlet port 1007 and a second outlet port 1008 communicated with the second balancing compartment 1004. At these ports each are provided a control valve 1009 (only one control valve is marked in FIG. 9) to close or open the respective port. The first inlet port 1005 and the second outlet port 1008 are interfaced via the membrane to fill fluid into the first balancing compartment and dispense fluid in the second balancing compartment 1004 to refresh fluid in the second chamber 105 with circulation of the amount of chamber volume, and, similarly the first outlet port 1006 and the second inlet port 1007 are interfaced via the membrane to fill regenerated fluid into the second balancing compartment 1004 and dispense dispensed fluid in the first balancing compartment to the fourth chamber 109 with circulation flow of the amount of the chamber volume.

With the balancing device 1002, fluid balance on patient side can be achieved by driving fluid into the first balancing compartment 1002 and driving fluid out of the second balancing compartment 1004 concurrently until the first balancing compartment 1003 is completely filled up. The first inlet port 1005 and the second outlet port 1008 will be opened by respective valves of 1008 to allow fluid flow in this step. In the next step, the first outlet port 1006 and the second inlet port 1007 are opened by respective valves of 1008 to fill regenerated fluid into the second balancing compartment 1004 while dispensed fluid from patient side will be passed to the fourth chamber 9 to be refreshed. In the closed system, fluid inflow toward the balancing chamber and fluid flow out of the balancing chamber are equal. Therefore, there is no uncontrollable fluid transfer between the patient 2 and the fluid regeneration device 114. Further, accurate flow of the third fluid in the circulation means 111 can be achieved by controlling the balancing device 1002, for example a rate of flow cycles of the balancing device 1002.

Specifically, the circulation means 111 comprises a first interface media circulation loop 1015 for the first dialysis device 101, and a second interface media circulation loop 1016 for the second dialysis device 102, wherein the first interface media circulation loop 1015 is connected fluidly with the second interface media circulation loop 1016 by the balancing device 1002, such that the interface media in the first interface media circulation loop 1015 and the interface media in the second interface media circulation loop 1016 can be exchanged in a controllable manner.

The first interface media circulation loop 1015 is configured to dispense the used interface media from the first dialysis device 101 to the first balancing compartment 1003 of the balancing device 1002 and the second interface media circulation loop 1016 is configured to fill the cleaned interface media from the second dialysis device 102 to the second balancing compartment 1004 of the balancing device 1002.

According to one exemplary embodiment of the present disclosure, the ultrafiltration means 1001 is connected fluidly with the first interface media circulation loop 1015.

The single balancing chamber can be driven by the driving device. In this case, the driving device preferably comprises a first pump 1010 configured to drive the first balancing compartment 1003 and a second pump 1011 configured to drive the second balancing compartment 1004.

The operational principle and process of the single balancing chamber are well known and thus are not described in detail herein.

According to one exemplary embodiment of the present disclosure, the circulation means 111 further comprises an air detection means 1012, configured to detect the presence of air in an air separation chamber 1013. The air detection means 1012 is preferably connected fluidly in the circulation loop of the third fluid. The air separation chamber 1013 is configured to remove the air from the air separation chamber 1013 via a valve or a peristatic pump connected on top of the air separation chamber 1013 after the air is detected.

According to one exemplary embodiment of the present disclosure, the air detection means 1012 and the air separation chamber 1013 are disposed but not limited in the second interface media circulation loop 1016.

According to one exemplary embodiment of the present disclosure, the air separation chamber 1013 can be configured to dispense waste fluid in both the first and second interface media circulation loops to allow for filling the fresh interface media and carry out priming the second chamber 105 and the fourth chamber 109.

Preferably, the air detection means 1012 is disposed or integrated in the air separation chamber 1013.

According to one exemplary embodiment of the present disclosure, the circulation means 111 further comprises a container 1014 fluidly connected with the circulation loop of the third fluid and configured to provide a fresh third fluid as desired.

Due to fluid balance control nature in the circulation loop of the third fluid, ultrafiltration can simply be done with the ultrafiltration means preferably during the dead time of the balancing device in connection to the first interface media circulation loop 1015. The fluid from the ultrafiltration mean can be disposed to a drain bag directly.

Figure 10:
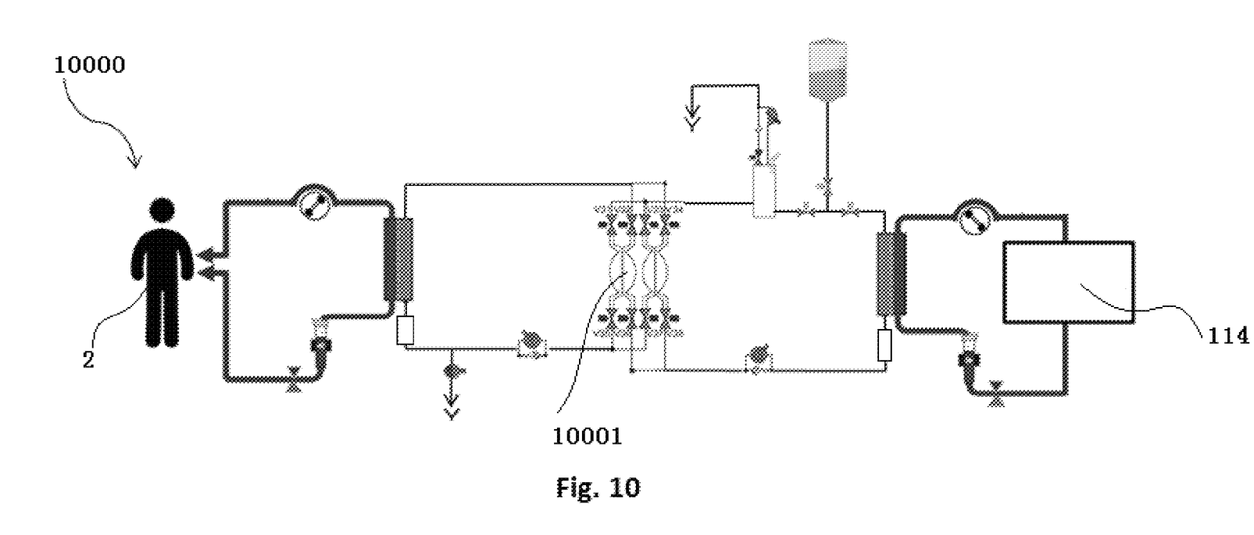
FIG. 10 shows a further dialysis system according to an exemplary embodiment of the present disclosure.

FIG. 10 shows a further dialysis system 10000 according to an exemplary embodiment of the present disclosure.

It may be seen by comparing FIG. 9 with FIG. 10 that the dialysis system 10000 shown in FIG. 10 differs mainly from the dialysis system 1000 shown in FIG. 9 in using a different balancing device. Specifically, the balancing device has dual balancing chambers 10001, each of which comprises a first balancing compartment and a second balancing compartment. Dual balancing chamber device is able to carry out dispensing and filling of the two circulation loops in parallel and thus can increase circulation flow rate to achieve optimal dialysis efficiency in the case that blood flow rate is high.

The operational principle and process of the dual balancing chambers also are well known and thus are not described in detail herein.

As can be seen from the above, the present disclosure actually also provides a method for establishing the dialysis system.

Furthermore, the present disclosure further provides a method for filling and/or priming the dialysis system.

According to one exemplary embodiment of the present disclosure, the method for filling and/or priming the dialysis system comprises filling the third fluid in a circulation loop of the third fluid with fluid volume of the balancing chamber in each cycle; and circulating the third fluid in the circulation loop for preset cycles per minute.

According to one exemplary embodiment of the present disclosure, the method for filling and/or priming the dialysis system further comprise repeating the filling and the circulating as necessary to refresh the third fluid in the circulation loop.

In addition, the present disclosure further provides a method for removing air from the dialysis system.

According to one exemplary embodiment of the present disclosure, the method for removing air from the dialysis system further comprises: turning off the balancing device on completion of a current cycle after air is detected; and filling a fresh third fluid in the air separation chamber until no air is detected.

According to the present disclosure, the dialysis device and the dialysis system are suitable for using the viscous biological dialysis fluid and prevent direct flow between the patient and the biological dialysis fluid, which allows for safer isolation in case abnormality is detected.

While certain embodiments have been described, these embodiments have been presented by way of example only, and are not intended to limit the scope of the disclosure. The attached claims and their equivalents are intended to cover all the modifications, substitutions and changes as would fall within the scope and spirit of the disclosure.

The invention claimed is:

1. A dialysis system comprising:
an electrolyte solution;
a first membrane comprising at least a first plurality of hollow fibers;
a second membrane comprising at least a second plurality of hollow fibers;
a first chamber formed by the first membrane, the first chamber being configured to receive a first fluid;
a second chamber formed by the second membrane, the second chamber being configured to receive a second fluid;
a third chamber formed in between a housing, the first membrane, and the second membrane, the third chamber being configured to receive the electrolyte solution;
a dialysate regeneration device fluidly coupled to the second chamber, the dialysate regeneration device configured to regenerate the second fluid after the second fluid passes through the second chamber;
a pump fluidly coupled to the third chamber, the pump configured to recirculate the electrolyte solution from an inlet port coupled with the housing at a first end of the third chamber to an outlet port coupled with the housing at a second end of the third chamber, wherein the second end is opposite the first end; and
a blood detector fluidly coupled to the third chamber, the blood detector configured to detect a blood leak into the electrolyte solution,
wherein a material and a structure of each fiber of the first plurality of hollow fibers are the same as those of the second plurality of hollow fibers.

2. The dialysis system according to claim 1, wherein:
the first plurality of hollow fibers are configured as a first bundle of hollow fibers, and the second plurality of hollow fibers are configured as a second bundle of hollow fibers separate from the first bundle of hollow fibers.

3. The dialysis system according to claim 1, wherein a number of fibers of the first plurality of hollow fibers is different from a number of fibers of the second plurality of hollow fibers.

4. The dialysis system according to claim 1, wherein:
the first fluid is a patient's or animal's blood to be treated; and/or
the second fluid is a biological dialysis fluid.

5. The dialysis system according to claim 1, wherein the dialysis system further comprises:
at least a first pair of ports coupled to the housing and configured to be communicated with the first chamber;
at least a second pair of ports coupled to the housing and configured to be communicated with the second chamber; and
at least a third pair of ports coupled to the housing and configured to be communicated with the third chamber, the third pair of ports comprising the inlet port and the outlet port.

6. The dialysis system according to claim 1, wherein:
a direction of the first fluid flowing through the first plurality of hollow fibers is opposite to that of the second fluid flowing through the second plurality of hollow fibers; or
the electrolyte solution fully fills the third chamber.

7. The dialysis system according to claim 1, wherein the first fluid flowing through the first membrane can be indirectly communicated with the second fluid flowing through the second membrane via the electrolyte solution.

* * * * *